(12) United States Patent
Gue et al.

(10) Patent No.: US 6,854,830 B2
(45) Date of Patent: Feb. 15, 2005

(54) THERMAL INJECTION AND PROPORTIONING HEAD, MANUFACTURING PROCESS FOR THIS HEAD AND FUNCTIONALIZATION OR ADDRESSING SYSTEM COMPRISING THIS HEAD

(75) Inventors: Anne-Marie Gue, Rebigue (FR);
Daniel Esteve, Ramonville (FR);
Véronique Conedera, Toulouse (FR);
Norbert Fabre, Lavaur (FR)

(73) Assignee: Brevalex, Paris (FR)

( * ) Notice: Subject to any disclaimer, the term of this patent is extended or adjusted under 35 U.S.C. 154(b) by 0 days.

(21) Appl. No.: 10/332,240

(22) PCT Filed: Jul. 12, 2001

(86) PCT No.: PCT/FR01/02274
§ 371 (c)(1),
(2), (4) Date: Jan. 3, 2003

(87) PCT Pub. No.: WO02/05946
PCT Pub. Date: Jan. 24, 2002

(65) Prior Publication Data
US 2004/0090483 A1 May 13, 2004

(30) Foreign Application Priority Data
Jul. 13, 2000 (FR) .............................................. 00 09195

(51) Int. Cl.[7] ................................................. B41J 2/05
(52) U.S. Cl. ........................................................ 347/61
(58) Field of Search ............................. 347/61, 57, 54, 347/68, 20, 40, 70, 71, 72, 175, 176; 216/4; 29/890.1; 430/311

(56) References Cited

U.S. PATENT DOCUMENTS 6,527,370 B1 * 3/2003 Courian et al. ............... 347/47

FOREIGN PATENT DOCUMENTS

| DE | 42 14 554 A1 | 11/1993 |
| DE | 42 14 555 A1 | 11/1993 |
| DE | 42 14 556 A1 | 11/1993 |
| EP | 0 530 209 A1 | 11/1991 |

* cited by examiner

Primary Examiner—Raquel Yvette Gordon
(74) Attorney, Agent, or Firm—Foley & Lardner LLP

(57) ABSTRACT

Injection and proportioning head with at least one thermal injection and proportioning device to supply a determined quantity of liquid, comprising:
  a hollowed out plane substrate (21) forming a liquid reservoir and covered, in order, by an unconstrained dielectric insulating membrane (22, 23) with a high thermal resistance, and then an etched semi conducting layer forming the heating resistance (25);
  an orifice (24) enabling fluid communication with said liquid reservoir passing through said membrane and said semi conducting layer;
  a photolithographed resin layer in the form of a nozzle (27) on said membrane, the duct (28) of said nozzle being in line with said orifice and the volume of said duct being such that the determined quantity of the liquid to be supplied can be controlled.

Process for manufacturing this head.

Functionalisation or addressing system, particularly for chemical or biochemical micro reactors comprising this head.

26 Claims, 4 Drawing Sheets

THERMAL INJECTION AND PROPORTIONING HEAD, MANUFACTURING PROCESS FOR THIS HEAD AND FUNCTIONALIZATION OR ADDRESSING SYSTEM COMPRISING THIS HEAD

DESCRIPTION

This invention relates to a thermal injection and proportioning head, and more precisely a thermal injection and proportioning head comprising at least one thermal injection and proportioning device with nozzle to supply and deliver a determined quantity of liquid.

The invention also relates to a manufacturing process for such a head.

Finally, the invention relates to a functionalisation or addressing system comprising such a head, particularly for biological or chemical micro reactors.

The invention is generally within the field or devices used to deposit several micro drops of a determined volume of liquid onto a substrate, or to add or inject several micro drops into micro reservoirs.

For example, these liquid drops may be DNA solutions of immunology reagents, which form miniaturized rows or matrices of drops or test reservoirs, which are used particularly for medical analyses.

For example, it is known that biochips are devices that can be used to make a very large number of bio analyses in parallel. The principle is to make test micro reservoir matrices in miniaturized form.

Each test point is specific and is the result of a precise mix or combination of chemical or biochemical elements. These mixes or combinations may be made by several processes, which may have been classified in two main categories.

In the first category of these processes called biochip functionalisation processes, the constituents are applied one by one and the reactions are checked by addressing an action to facilitate or inhibit the reaction on targeted micro reservoirs.

In the second category of biochip functionalisation processes, the specific constituents are added point by point mechanically into the targeted micro reservoir; the domain of the invention is related to this second category.

Biochip functionalisation processes are divided between firstly "in situ" processes and secondly "ex situ" processes.

The AFFIMETRIX® process is the main in situ synthesis process, in other words for example the synthesis of a DNA strand, and is done directly on the chip, on a solid support. This process is based on in situ synthesis, in other words directly on the chip, of trace nucleotides, for example DNA strands, with methods derived from photolithography.

The surfaces of hybridisation units (UH), modified by a photolabile protective group, are illuminated through a photolithography mask. UHs thus exposed to light radiation are selectively deprotected and can therefore be subsequently coupled to the next nucleic acid. The deprotection and coupling cycles are repeated until all required trace nucleotides are obtained.

Experiments have already been carried out with other EX SITU processes using the microelectronic capacities of silicon. The chip comprises several platinum microelectronic electrodes, placed in the bottom of dishes machined in silicon and addressed individually. The probes, such as trace nucleotides or DNA strands are coupled to a pyrrole group and are directed by an electric field to the activated electrode, where copolymerisation takes place in the presence of free pyrrole and the result is electrochemical bonding of the probes.

Based on the above, it appears that in situ synthesis processes such as AFFIMETRIX® are used to achieve high densities of hybridising units and use perfectly controlled techniques compatible with silicon supports. Their major disadvantages are their high cost which makes it impossible for small entities such as research laboratories or medical analysis laboratories to use them, and the fact that the low efficiency of the photodetection reaction means that there is a great deal of redundancy in the sequences present on the chip.

Manufacture is relatively difficult particularly due to the photolithographic masks and is therefore adapted particularly to targeted objectives with high usage volumes.

In "ex situ" processes, in other words processes in which the DNA strand is synthesised ex situ, each sequence must be pre-synthesised independently of the others and then transferred to the support. The procedure is long and it is impossible to make a large number of different sequences on the same chip. The chips made will thus be low density chips.

The second category of addressing processes, that can be qualified as mechanical addressing processes regardless of whether they are ex situ or in situ, is represented by many processes that are already marketed, in which robotized, for example pneumatically activated, micropipettes assembled in matrix form, pick up constituents (generally a solution containing DNA fragments or trace nucleotides) and deposit them in the form of precise doses, for example micro drops in test tubes or on miniaturized supports. Glass slides are usually used as support, or structured supports may be used supporting micro wells etched in the material. Each of the bases (A, G, C, T) can also be deposited in sequence on the glass slide in the required order.

These conventional techniques are typically used in 96-pin matrices, and higher densities are possible. The objective with these mechanical processes would be to reach 10 000 dots or more, since there is a large number of tests to be carried out in parallel. The number of pins on the same wafer may be as high as 8000.

The production of micro reservoir matrices is a simple problem that can easily be solved by microelectronic technologies. We can make:

simple substrates comprising matrices micro-machined by chemical or plasma means. Densities of the order of 10 000 dots/cm$^2$ are typical, but 100 000 dots/cm$^2$ are also possible;

substrates instrumented by electronic or electromechanical systems; the MICAM chip marketed by the Cis-Bio® Company is a good example of these substrates. This is the (ex situ) process illustrated in the first case above.

The more difficult problem is actually to deposit the reagents (probes or others) specifically in each micro reservoir. Several techniques are used for pipetting, including deposition by "pin and ring" by capillary contact; deviated continuous piezoelectric "ink jet" or "drop on demand", or thermal ink jet.

The technique used in thermal ink jet printer heads is very widespread and very reliable.

In general, a thermal ink jet printer head, for example acting as a thermal proportioner micro injector, satisfies the operating principle described below.

The liquid to be ejected is confined in a reservoir.

A heating resistance very locally increases the temperature in the reservoir and vaporizes the liquid in contact with the heating area. The gas bubble thus formed creates an overpressure that ejects a drop outside the reservoir.

FIG. 1 ideally performs this function.

Under the effect of pressure and capillarity forces, the nozzle (1) with radius r (6) is filled with liquid from a reservoir (4). The nozzle is surrounded by a heat input system at a depth L (2), for example a heating resistance (5) operating by the Joule effect.

Under the effect of the temperature increase at the level (3) and the vaporization of volatile species of the liquid, the top part of the liquid is ejected forming a drop with size $v=\pi r^2 L$, where r is the radius (6) of the nozzle (1) and L is the height of the liquid column corresponding to the depth (2).

Operation is possible continuously, and enables the production of a sequence of drops. Operation is also possible drop by drop. The internal radius of the nozzle and its height L are controlled so that drops of the order of one picoliter can be produced with injection densities of $10^5$ to $10^2/cm^2$. The hole density is important because there is no thermal interaction from one hole to the next.

There are three main types of thermal ink jet printer head devices that apply the principle described above illustrated in FIG. 1.

The first of these devices is the "EDGESHOOTER" device in which two substrates, one made of silicon supporting the heating element and one made of glass, are combined using a glued film and structured by photolithography. Drops are ejected laterally on the edge of the device.

The second is the "SIDESHOOTER" device for which the structure, similar to the structure of the previous device, comprises a silicon substrate and a glued film, but which are covered by a metallic plate on which the nozzles are made. Drops are ejected facing the heating element.

The third is the "BACKSHOOTER" device in which the print head is made from oriented silicon substrates <110>.

The ducts through which the ink passes are made by anisotropic etching of one side of the substrate, while thin films are deposited on the other side that enable production of the membrane supporting the heating element and the electronics. The nozzles are located at the centre of the membrane and the heating elements are located on each side of the membrane. Resolution can be as high as 300 dpi (dots per inch) and 600 dpi.

In all cases, in other words for the three devices, the print head is composed of a single line comprising only about fifty nozzles each about 20 µm×30 µm. The velocity of the drops at ejection varies from 10 to 15 m/s.

For example, this type of device is described in documents PCT/DE 91/00364, EP-A-0 530 209, . . . DE-A-42 14 554, DE-A-42 14555 and DE-A-42 14556.

All these thermal ink jet print head devices, particularly when used for an application such as a thermal proportioning micro injector head, have the serious disadvantage of large heat losses.

Consequently, it is only possible to make heads with a single line of holes rather than a matrix. Therefore, the densities and resolutions are not nearly sufficient.

Therefore, there is a need for an injection and proportioning head comprising a thermal injection and proportioning device that does not have this serious disadvantage.

There is also a need for an injection and proportioning head that can achieve densities and resolutions at least equivalent to those obtained with in situ addressing or synthesis systems such as AFFIMETRIX® without having these disadvantages. At the moment, no mechanical addressing system is capable of achieving these densities and resolutions.

The purpose of this invention is to provide an injection and proportioning head for a thermal injection proportioning device which, among others, satisfies all the needs mentioned above.

Another purpose of this invention is to provide a thermal injection and proportioning head that does not have the disadvantages, limitations, defects and drawbacks of injection and proportioning heads according to prior art and which solves the problems that arise for injection and proportioning heads according to prior art.

This and other purposes are achieved according to the invention by an injection and proportioning head comprising at least one thermal injection and proportioning device to supply a given quantity of liquid, said device comprising:

- a hollowed out plane substrate forming a liquid reservoir and covered, in order, by an unconstrained dielectric insulating membrane with a high thermal resistance, and then an etched semi-conducting layer forming the heating resistance;
- an orifice allowing fluid communication with said liquid reservoir passing through said membrane and said semi conducting layer;
- a layer of photolithographed resin in the form of a nozzle on said membrane, the duct for said nozzle being located along the same line as said orifice and the volume of said duct being used to control the quantity of liquid to be supplied.

According to the invention, heating is done on an unconstrained dielectric insulating membrane with a high thermal resistance, and consequently heat losses are very much reduced and as a result it will be possible to make a head comprising a two-dimensional matrix of nozzles or holes, rather than simply a simple line or row.

In other words, the structure of the device according to the invention comprising three layers on the substrate and which has never been mentioned in prior art is such that, surprisingly and optimally, the heat generated only very slowly passes through the membrane that has a high or very high thermal resistance. Thus one of the major disadvantages of similar devices according to prior art, namely high heat losses, is eliminated. Injection-proportioning devices in a head can be brought closer together and have a significantly higher density than in prior art. Thus, heads according to the invention can be used to make two-dimensional matrices of nozzles or injection-proportioning holes with a high density, for example $10^4/cm^2$.

Furthermore, the volume to be delivered and supplied in the device according to the invention is easily and very precisely determined by the volume of the nozzle duct and which is easily made from photolithographed resin.

The head according to the invention can supply perfectly defined quantities of liquid at perfectly defined points, for example with a density of $10^4$ to $10^5/cm^2$, which has never been achieved in the past with mechanical devices of the thermal micropipette type.

The determined quantity of liquid to be supplied and delivered by the device is usually between 1 and a few nl, up to 100 µl. This is why the term "micropipette" is generally used.

The substrate is generally made of monocrystalline silicon, possibly doped.

Advantageously, according to the invention, the unconstrained dielectric insulating membrane with a high thermal resistance is composed of a stack of two layers, with thicknesses such that the (thermo)mechanical stress in the stack is zero.

The membrane can thus be composed of a stack of a first layer of $SiO_2$ on the substrate, followed by a second layer of $SiN_x$ where x is preferably 1.2.

For example, the semi-conducting layer could be polysilicon or doped polycrystalline silicon. The doping element could advantageously be phosphorus.

It is also possible to provide a chemically and thermally insulating layer between the etched semi-conducting layer forming a heating resistance and the layer of photolithographed resin in the form of a nozzle.

Advantageously, the head according to the invention comprises several of said thermal injection and proportioning devices.

Preferably, this is made possible by the structure of the device according to the invention, said devices and consequently the holes or nozzles are arranged in the form of a two-dimensional matrix.

When the head comprises several thermal injection and proportioning devices, the number of these devices may for example be $10^2$ to $10^5$ for a head area of 10 $mm^2$ to 1.5 $cm^2$.

Advantageously, the head according to the invention is formed entirely from a single substrate; from a single insulating membrane, semi-conducting layer and photolithographed resin layer.

The invention also relates to a process for manufacturing an injection and proportioning head according to claim 1, in which the following steps are carried out in sequence:

- an unconstrained dielectric insulating layer or membrane with a high thermal resistance is made on the two faces of a plane substrate;
- a semi conducting layer is deposited on the dielectric insulating layers;
- a pattern of a photosensitive resin is made on a semi conducting layer located on the top face of the substrate, and then the areas of the unconstrained semi conducting layer not protected by resin are eliminated, thus making a heating resistance pattern;
- a chemically and thermally insulating layer may be made on the top face of the substrate;
- an orifice is made in the semi-conducting layer, in the unconstrained dielectric insulating layer with a high thermal resistance on the top face of the substrate, and possibly in the chemically and thermally insulating layer;
- a thick layer of photosensitive resin is deposited on the top face of the substrate and it is photolithographed to make a nozzle in line with the orifice;
- openings are made in the dielectric insulating layer on the back of the substrate;
- the areas of the back face of the substrate not protected by the dielectric insulating layer are etched, in order to create a reservoir for the liquid to be ejected and to release the membrane.

The substrate may be made of a monocrystalline silicon, possibly doped.

Advantageously, the dielectric insulating membrane is made by successively depositing two layers forming a stack on the substrate, the thicknesses of the two layers being such that the (thermo)mechanical stress in the stack is zero.

The first layer may be a layer of $SiO_2$ and the second layer may be a layer of $SiN_x$.

The semi conducting layer is generally made of polysilicon or polycrystalline silicon, preferably doped by phosphorus.

The areas of the semi conducting layer not protected by the photosensitive resin are preferably eliminated by a plasma etching process.

The heating resistance pattern is usually in the form of a square surrounding the ejection head, but it may also have any geometry enabling a local but sufficient temperature increase.

The chemically and thermally insulating layer is usually made of a layer of silicon oxide, of the Spin On Glass (SOG) type.

The orifice or hole in the chemically and thermally insulating layer (if there is such a layer), in the semi-conducting layer and in the dielectric insulating layer may be made by a chemical etching and/or plasma etching process depending on the layer.

The openings in the dielectric insulating layer on the back face of the substrate are preferably made by photolithography.

The unprotected areas of the back face of the substrate are usually etched by a chemical process, but may be etched by plasma.

Finally, the invention relates to a functionalisation or addressing system, particularly for chemical or biochemical micro reactors comprising the ejection and proportioning head described above.

In this type of system, the proportioned injected liquid may for example be a solution of reagents such as phosphoramidites, etc.

This type of system according to the invention overcomes the difficulties mentioned above for such systems either of the "in situ" or "ex situ" type.

In particular, systems according to the invention in which the heads comprise injection device matrices and therefore nozzles have the following advantages:

- the possibility of functionalising a large number of small hybridisation units (<100 $\mu$m×100 $\mu$m) in parallel;
- use of the chemical method and therefore improvement of synthesis yields;
- flexibility of the device to make the required sequences on request, without any cost effectiveness threshold problem;
- low cost.

At the present time, the use of biochips is limited to a few large companies. The system according to the invention makes this use possible by all potential customers.

Thus, apart from genomics or biochips, heads and systems according to the invention can be used in combinational chemistry or pharmaceutical formulation applications.

The invention will now be described in detail. The following description is given for illustrative and non limitative purposes with reference to the appended drawings, wherein.

Figure 1:
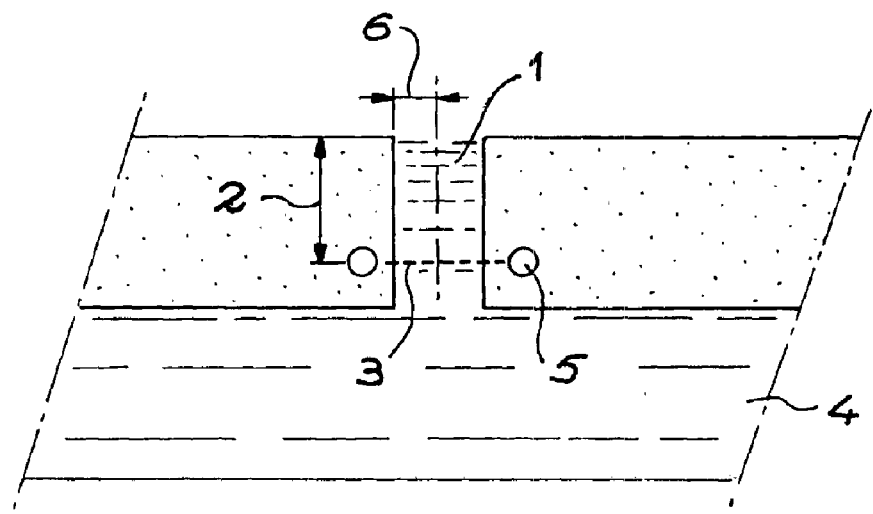
FIG. 1 is a diagrammatic sectional view of an ideal theoretical device for a thermal proportioning micro injector.
Figure 2:
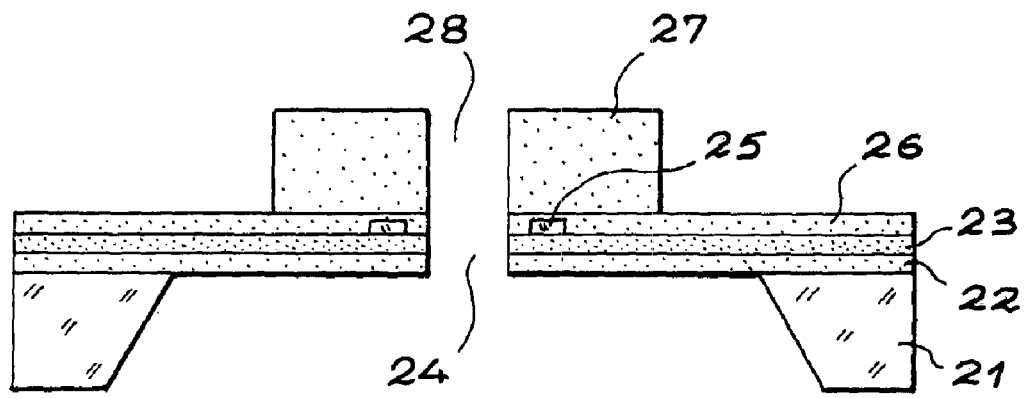
FIG. 2 is a diagrammatic sectional view of a thermal proportioning micro injector according to the invention.

The structure of the thermal proportioning micro injector in FIG. 2 comprises firstly a monocrystalline silicon support (11), preferably a monocrystalline silicon doped by an element, particularly such as chemical etching of silicon, in basic solutions if possible.

For example, the doping element may be chosen among boron and phosphorus.

There is a membrane on the support composed of a first insulating layer of $SiO_2$ (22) and a second layer of $SiN_x$ (23) where x=1.2. The relative thickness of each of these insulating layers is controlled such that there is very little and preferably no residual mechanical stress with the monocrystalline silicon support.

Furthermore, the thickness of the $SiN_x$ layer is preferably such that the residual mechanical stress resulting from the stack of these two layers is theoretically zero.

The thickness of the $SiO_2$ layer is usually 0.8 to 1.6 μm, whereas the thickness of the $SiN_x$ layer is usually 0.2 to 0.9 μM.

A small hole (24) is formed in this membrane. This hole is usually circular, for example with a diameter from 5 to 50 microns.

The membrane supports an integrated heating resistance (25), usually made of strongly doped polycrystalline silicon in order to achieve the lowest possible electrical resistivity.

The doping element of this polycrystalline silicon will for example be chosen from among phosphorus and boron with a content of $10^{19}$ to $10^{20}$ at/cm$^3$.

This type of heating resistance may locally warm up to high temperatures of up to several hundred of degrees, for example from 40 to 500° C.

The heating resistance is thermally and chemically insulated, preferably by a layer of silicon oxide (26), for example a "spin on glass" type layer of silicon oxide.

A nozzle is added onto the insulating silicon oxide layer, this nozzle (27) is usually made from a photosensitive resin such as SV8 resin (CIPEC®), due to the manufacturing process used.

The duct (28) of the nozzle (27) is in line with the hole made in the membrane and the insulating layer, for example made of silicon oxide.

The manufacturing process according to the invention comprises the following steps illustrated in FIGS. 3 to 12:

1. The substrate or nozzle support (21) is a double sided polished silicon wafer, for example 350 to 500 μm thick with dimensions 10 to 15 cm. The dimensions of the wafer are large enough to make 50 to 1000 thermal proportioning micro injectors. As already mentioned above, it is a monocrystalline silicon support, preferably doped by an element such that chemical etching of the doped silicon is possible, particularly in basic solutions such as KOH or TMAH. Therefore the doping element may be chosen from among boron or phosphorous, with a content of $10^{16}$ to $10^{18}$ at/cm$^3$.

Figure 3:
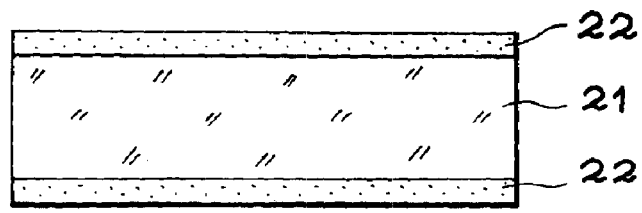
FIGS. 3 to 12 are diagrammatic sectional views that illustrate the different steps in the process according to the invention.

2. A silicon oxide layer (22), for example with a thickness between 0.8 and 1.6 μm, is made on the two faces of the wafer (FIG. 3).

The oxide layer (22) is obtained by direct oxidation of silicon, usually at a temperature of 1150° C.

Figure 4:
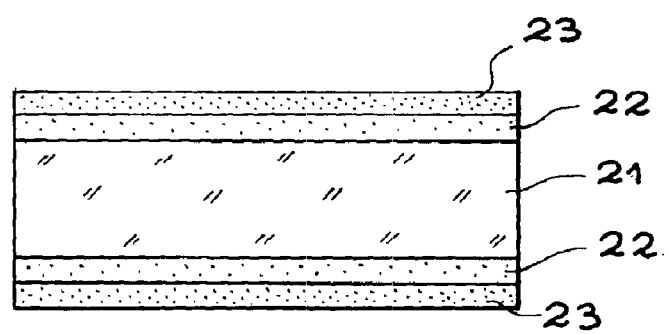

3. A layer of $SiN_x$ (23) is then deposited on the two faces of the wafer (FIG. 4). In the formula $SiN_x$, x is a real number x=1.2. The thickness of this layer is such that the residual mechanical stress resulting from the stack of the $SiO_2$ layer and the $SiN_x$ layer is theoretically zero. Thus, the thickness of the $SiN_x$ layer is usually between 0.2 and 0.9 μm.

The deposit is usually made using a vapour phase deposition technique.

The layers of $SiO_2$ and $SiN_x$ present on the back face of the silicon wafer will be used at the end of masking layer manufacturing process during chemical etching to release the membrane.

Figure 5:
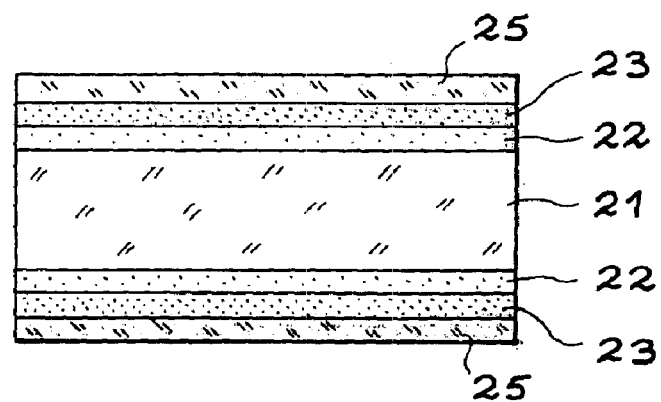

4. A layer of polysilicon or polycrystalline silicon (25) is then deposited on the two faces of the wafer (FIG. 5). The thickness of this layer is usually between 0.5 and 1.5 μm. The deposit is usually made using a vapour phase deposition technique.

This layer (25) is then doped, for example by diffusion of phosphorus to achieve the lowest possible electric resistivity. Therefore, the content of a doping agent such as phosphorus in the polysilicon layer (25), will usually be between $10^{19}$ and $10^{20}$ at/cm$^3$. The diffusion doping operation is usually done under the conditions T=950° C. for 25 minutes.

5. The polysilicon layer deposited in step 4 is covered with a photosensitive resin (29) in a square pattern and over a thickness of for example 1 to 3 μm. For example, this photosensitive resin may be chosen from among CLARIANT resins.

The photosensitive resin (29) is generally deposited using a centrifugal deposition technique.

The photosensitive resin (29) is selectively etched using a photolithography technique. Polysilicon areas not protected by the resin are eliminated by plasma etching.

Figure 6:
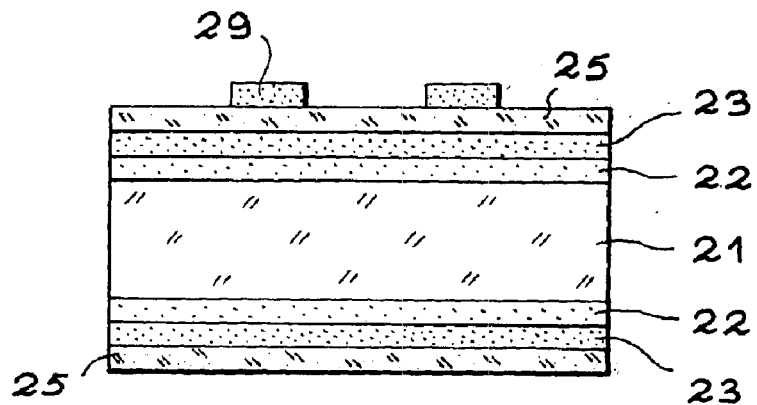
Figure 7:
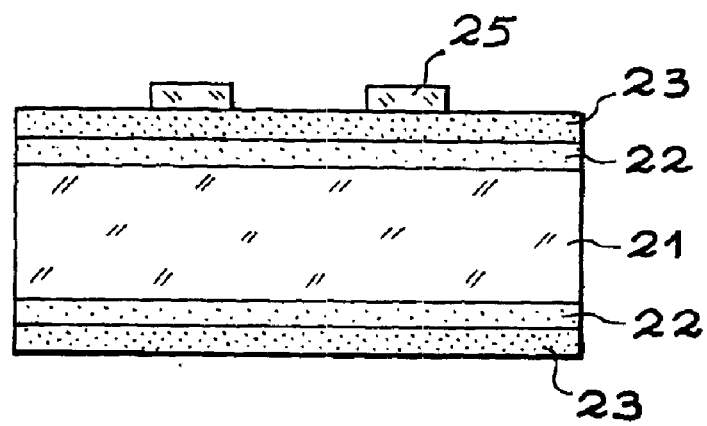

The pattern thus formed is used to make a heating resistance approximately in the form of a ring (FIGS. 6 and 7).

Figure 8:
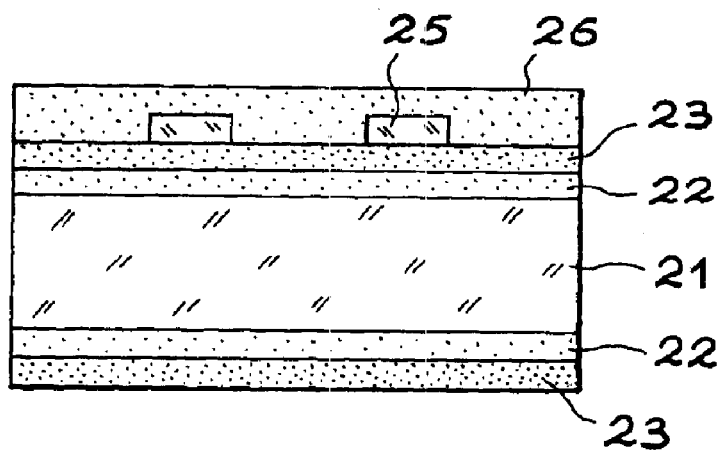

6. For example, the polysilicon resistance is covered with a spin on glass type silicon oxide layer (26), usually 100 to 200 nm thick, so that it is electrically and chemically protected from the outside environment (FIG. 8).

Figure 9:
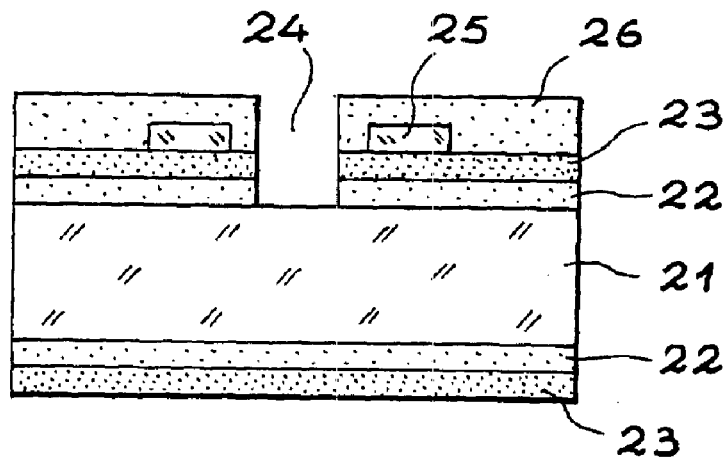

7. A hole (24) that will form the ejection orifice, is made at the centre of the heating resistance by chemical etching, for example, in a HF solution of silicon oxide ("spin on glass") then plasma etching of $SiN_x$ and then once HF chemical etching of the silicon oxide layer (FIG. 9).

This hole (24) is usually circular and has a diameter of between 5 and 50 μm.

8. A thick layer of photosensitive resin (27) is based on the spin on glass silicon oxide layer (26). A thick layer usually means a layer with a thickness of between 1 μm and 100 μm.

The photosensitive resin is usually the SV8 resin made by CITEC® and the deposition technique is deposition by centrifuging.

Figure 10:
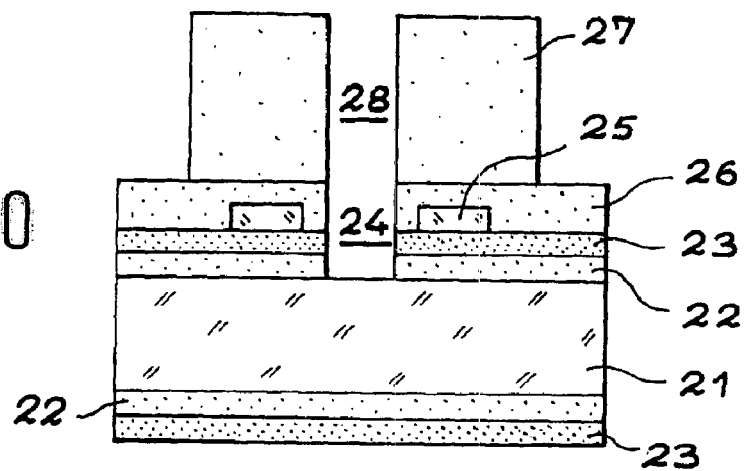

After the deposition, the resin layer is photolithographed in order to make the ducts (28) of the nozzles surrounding the hole or injection orifice (FIG. 10).

Figure 11:
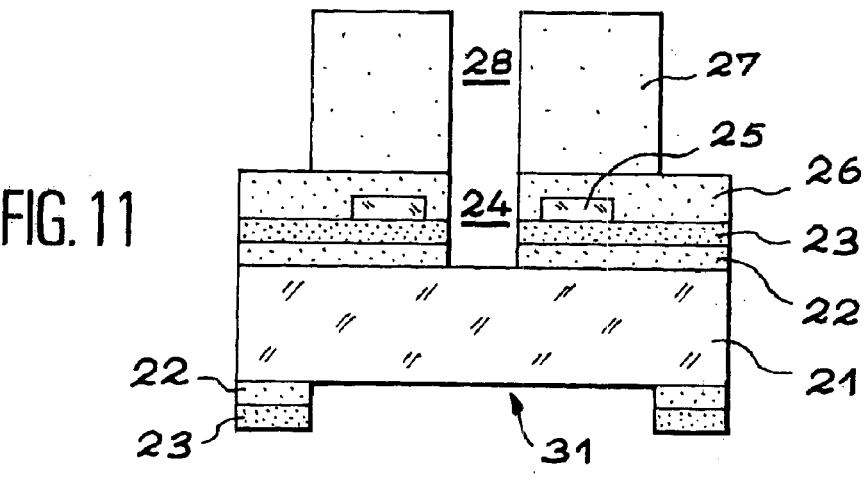

9. Openings (31) are formed in the $SiO_2$ and $SiN_x$ layers present on the back face using a photolithography process, already presented above (FIG. 11).

Figure 12:
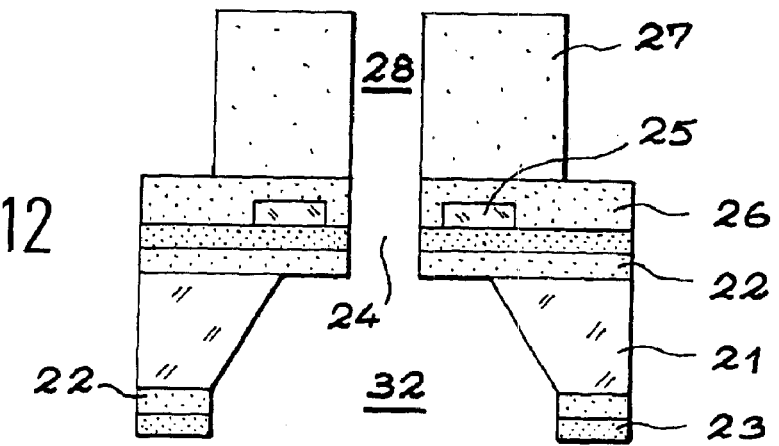

10. Chemical etching of areas not protected by the $SiO_2$/$SiN_x$ double layer, for example in a solution of KOH or TMAH, firstly excavates the reservoir (32) in the silicon substrate, to hold the liquid to be injected and also releases the membrane supporting the heating device and the ejection nozzle (FIG. 12).

What is claimed is:

1. An injection and proportioning head comprising at least one thermal injection and proportioning device to supply a determined quantity of liquid, said device comprising:
   a hollowed out plane substrate (21) forming a liquid reservoir and covered, in order, by
      a directly deposited unconstrained dielectric insulating membrane (22, 23) with a high thermal resistance,
      a directly deposited etched semi conducting layer forming the heating resistance (25);
      an orifice (24) enabling fluid communication with said liquid reservoir passing through said membrane and said semi conducting layer, and thereafter
      a photolithographed resin layer in the form of a nozzle (27) on said membrane, the duct (28) of said nozzle being in line with said orifice and the volume of said duct being such that the determined quantity of the liquid to be supplied can be controlled.

2. Injection and proportioning head according to claim 1, in which the determined quantity of liquid is 1 nl to 100 μl.

3. Head according to claim 1, in which the substrate comprises monocrystalline silicon.

4. Head according to claim 1, in which the semi conducting layer is made of doped polysilicon or polycrystalline silicon.

5. Head according to claim 4, in which the polysilicon or the polycrystalline silicon is doped by phosphorus.

6. Head according to claim 1, in which a chemically and thermally insulating layer is also provided between the etched semi conducting layer and the photolithographed resin layer in the form of a nozzle.

7. Head according to claim 1, comprising several thermal injection and proportioning devices.

8. Head according to claim 7, in which said devices are arranged in the form of a two-dimensional matrix.

9. Head according to claim 7, comprising $10^2$ to $10^5$ injection devices.

10. Head according to claim 7, in which the head is formed entirely from a single substrate; from a single insulating membrane, semi conducting layer, a chemically and thermally insulating layer if there is one, and a photolithographed resin layer.

11. Functionalisation or addressing system, particularly for chemical or biochemical micro reactors, comprising the injection and proportioning head according to claim 1.

12. Use of the system according to claim 11 in techniques using biochips, genomics, combinational chemistry of pharmaceutical formulation.

13. Use of the head according to claim 1, in techniques involving biochips, genomics, combinational chemistry or pharmaceutical formulation.

14. Head according to claim 1, in which the substrate comprises doped monocrystalline silicon.

15. An injection and proportioning head comprising at least one thermal injection and proportioning device to supply a determined quantity of liquid, said device comprising:
   a hollowed out plane substrate (21) forming a liquid reservoir and covered, in order, by
   an unconstrained dielectric insulating membrane (22,23) with a high thermal resistance composed of a stack of two layers, the thickness of which are such that the (thermo)mechanical stress in the stack is zero,
   an etched semi conducting layer forming the heating resistance (25),
   an orifice (24) enabling fluid communication with said liquid reservoir passing through said membrane and said semi conducting layer,
   a photolithographed resin layer in the form of a nozzle (27) on said membrane, the duct (28) of said nozzle being in line with said orifice and the volume of said duct being such that the determined quantity of the liquid to be supplied can be controlled.

16. Head according to claim 15, in which the membrane is composed of a stack comprising, in order, a first layer of $SiO_2$ on the substrate, followed by a second layer of $SiN_x$, where x is preferably 1.2.

17. Manufacturing process for an injection and proportioning head according to claim 1, in which the following steps are carried out in sequence:
   an unconstrained dielectric insulating layer or membrane with a high thermal resistance is directly made on the two faces of a plane substrate;
   a semi conducting layer is directly deposited on the dielectric insulating layers;
   a pattern of a photosensitive resin is made on a semi conducting layer located on the top face of the substrate, and then the areas of the unconstrained semi conducting layer not protected by resin are eliminated, thus making a heating resistance pattern;
   a chemically and thermally insulating layer may be made on the top face of the substrate;
   an orifice is made in the semi-conducting layer, in the unconstrained dielectric insulating layer with a high thermal resistance on the top face of the inorganic plane substrate, and possibly in the chemically and thermally insulating layer;
   a thick layer of photosensitive resin is deposited on the top face of the substrate and it is photolithographed to make a nozzle in line with the orifice;
   openings are made in the dielectric insulating layer on the back of the substrate;
   the areas of the back face of the inorganic plane substrate not protected by the dielectric insulating layer are etched, in order to create a reservoir for the liquid to be ejected and to release the membrane.

18. Process according to claim 17, in which the substrate is made of monocrystalline silicon.

19. Manufacturing process for an injection and proportioning head according to claim 1, in which the following steps are carried out in sequence:
   an unconstrained dielectric insulating membrane is formed on both sides of the substrate forming a stack, the thickness of the two layers being such that the (thermo)mechanical stress of the stack is zero with a high thermal resistance is made on the top face and back face of a plane substrate;
   a semi conducting layer is deposited on the dielectric insulating membrane;
   a pattern of a photosensitive resin is made on a semi conducting layer located on the top face of the substrate, and then the areas of the semi conducting layer not protected by resin are eliminated, thus making a heating resistance pattern;
   a chemically and thermally insulating layer may be made on the face of the substrate;
   an orifice is made in the semi-conducting layer, in the unconstrained dielectric insulating membrane with a high thermal resistance on the top face of the plane substrate, and possibly in the chemically and thermally insulating layer;
   a thick layer of photosensitive resin is deposited on the top face of the substrate and it is photolithographed to make a nozzle in line with the orifice;
   openings are made in the dielectric insulating membrane on the back of the substrate;
   areas of the back face of the substrate are etched, in order to create a reservoir for the liquid to be ejected and to release the membrane.

20. Process according to claim 19, in which the first layer of the stack is an $SiO_2$ layer and the second layer is an $SiN_x$ layer wherein x is about 1.2.

21. Process according to claim 17, in which the semi conducting layer is made of doped polysilicon or polycrystalline silicon.

22. Process according to claim 17, in which the areas of the semi conducting layer not protected by the photosensitive resin are eliminated using a plasma etching process.

23. Process according to claim 17, in which the orifice in the chemically and thermally insulating layer, if any, in the semi conducting layer and in the dielectric insulating layer, is made using a chemical etching and/or plasma etching process, depending on the layer.

24. Process according to claim 17, in which the openings in the dielectric insulating layer on the back face of the substrate are made by photolithography.

25. Process according to claim 17, in which the unprotected areas on the back face of the substrate are etched by a chemical process.

26. Process according to claim 17, in which the substrate comprises doped monocrystalline silicon.

* * * * *